US012576214B2

(12) United States Patent
Collings et al.

(10) Patent No.: US 12,576,214 B2
(45) Date of Patent: Mar. 17, 2026

(54) BUTTON AND BUTTON ASSEMBLY FOR A DRUG DELIVERY DEVICE

(71) Applicant: Sanofi, Paris (FR)

(72) Inventors: Ralph Donald Quentin Collings, Bristol (GB); James Robert Coop, Bristol (GB); James Anthony West, Bristol (GB); Stephen Francis Gilmore, Bristol (GB); Daniel David Higgins, Bristol (GB); Mark Digby Teucher, Bristol (GB); Matthew Meredith Jones, Warwick (GB); Anthony Paul Morris, Warwick (GB); Sophie Sladen, Warwick (GB); William Geoffrey Arthur Marsh, Warwick (GB); Denny Lustosa Horn, Frankfurt am Main (DE); Stefan Blancke, Frankfurt am Main (DE); Michael Jugl, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 18/422,551

(22) Filed: Jan. 25, 2024

(65) Prior Publication Data

US 2024/0157060 A1 May 16, 2024

Related U.S. Application Data

(62) Division of application No. 16/760,121, filed as application No. PCT/EP2018/079640 on Oct. 30, 2018, now Pat. No. 11,918,794.

(30) Foreign Application Priority Data

Nov. 2, 2017 (EP) ..................................... 17306510
Jul. 17, 2018 (EP) ..................................... 18305967

(51) Int. Cl.
*A61M 5/315* (2006.01)
*H01H 3/12* (2006.01)
*A61B 17/00* (2006.01)

(52) U.S. Cl.
CPC .......... *A61M 5/31585* (2013.01); *H01H 3/12* (2013.01); *A61B 2017/00367* (2013.01);
(Continued)

(58) Field of Classification Search
CPC ..................... A61M 5/31585; A61M 5/31553; H01H 3/12; A61B 2017/00367
See application file for complete search history.

(56) References Cited

U.S. PATENT DOCUMENTS 5,820,602 A 10/1998 Kovelman et al.
6,835,906 B2 12/2004 Okamoto et al.
(Continued)

FOREIGN PATENT DOCUMENTS

CN 101262899 A 9/2008
CN 101563125 A 10/2009
(Continued)

OTHER PUBLICATIONS

International Preliminary Report on Patentability in Application No. PCT/EP2018/079640, dated May 5, 2020, 11 pages.
(Continued)

*Primary Examiner* — Emily L Schmidt
(74) *Attorney, Agent, or Firm* — BOND, SCHOENECK & KING PLLC

(57) ABSTRACT

A button for a drug delivery device with a reduced operating loudness includes a plate-like button body forming a touch surface, wherein the plate-like button body is coupled by an axial supporting member to a noise-generating interface of the drug delivery device and movable into a longitudinal direction of the drug delivery device, wherein the plate-like
(Continued)

button body includes a material composite with at least one first component consisting of a first material and at least one second component consisting of a second material different from the first material, wherein the at least one first component and the at least one second component are coupled via at least one coupling plane that is at least section wise slanted or perpendicular to the longitudinal direction. Further, the disclosure describes a button assembly for a drug delivery device which is shock resistant.

11 Claims, 9 Drawing Sheets

(52) U.S. Cl.
CPC ..... *A61M 2205/33* (2013.01); *A61M 2205/43* (2013.01); *A61M 2205/581* (2013.01); *A61M 2205/582* (2013.01)

(56) References Cited

U.S. PATENT DOCUMENTS

| | | | |
|---|---|---|---|
| 7,955,303 | B2 | 6/2011 | Burren et al. |
| 8,016,797 | B2 | 9/2011 | Gratwohl et al. |
| 11,918,794 | B2 | 3/2024 | Collings et al. |
| 2011/0270161 | A1 | 11/2011 | Harrison et al. |
| 2013/0018313 | A1 | 1/2013 | Kramer et al. |
| 2013/0190694 | A1 | 7/2013 | Barrow-Williams et al. |
| 2015/0018770 | A1 | 1/2015 | Baran et al. |
| 2015/0246181 | A1 | 9/2015 | Fourt et al. |
| 2015/0258284 | A1 | 9/2015 | Fenster et al. |
| 2016/0051768 | A1* | 2/2016 | Butler ............... A61M 5/31535 604/211 |
| 2017/0007764 | A1 | 1/2017 | Saussaye et al. |
| 2017/0151392 | A1 | 6/2017 | Marsh et al. |
| 2020/0330697 | A1 | 10/2020 | Collings et al. |

FOREIGN PATENT DOCUMENTS

| | | | |
|---|---|---|---|
| CN | 101827624 | A | 9/2010 |
| CN | 104602731 | A | 5/2015 |
| CN | 104602732 | A | 5/2015 |
| CN | 104684598 | A | 6/2015 |
| CN | 104703643 | A | 6/2015 |
| CN | 105492050 | A | 4/2016 |
| CN | 106102805 | A | 11/2016 |
| CN | 106132458 | A | 11/2016 |
| CN | 106659848 | A | 5/2017 |
| CN | 106794308 | A | 5/2017 |
| GB | 1206340 | A | 9/1970 |
| JP | 2007-510465 | A | 4/2007 |
| JP | 2017-518840 | A | 7/2017 |
| WO | WO 2005/046765 | A2 | 5/2005 |
| WO | WO 2009/019436 | A1 | 2/2009 |
| WO | WO 2009/114542 | A1 | 9/2009 |
| WO | WO 2012/110577 | A1 | 8/2013 |
| WO | WO 2014/033141 | A1 | 3/2014 |
| WO | WO 2014/033142 | A2 | 3/2014 |
| WO | WO 2014/033143 | A1 | 3/2014 |
| WO | WO 2014/033144 | A1 | 3/2014 |
| WO | WO 2014/062488 | A1 | 4/2014 |
| WO | WO 2015/028439 | A1 | 3/2015 |
| WO | WO 2015/101574 | A1 | 7/2015 |
| WO | WO 2015/197629 | A1 | 12/2015 |
| WO | WO 2016/001300 | A1 | 1/2016 |
| WO | WO 2016/055628 | A1 | 4/2016 |
| WO | WO 2016/055634 | A1 | 4/2016 |
| WO | WO 2016/120587 | A1 | 8/2016 |
| WO | WO 2016/141062 | A2 | 9/2016 |
| WO | WO 2017/009284 | A1 | 1/2017 |
| WO | WO 2017/025708 | A1 | 2/2017 |
| WO | WO 2017/037468 | A1 | 3/2017 |
| WO | WO 2017/144200 | A1 | 8/2017 |

OTHER PUBLICATIONS

International Search Report and Written Opinion in Application No. PCT/EP2018/079640, dated May 10, 2020, 16 pages.

* cited by examiner

BUTTON AND BUTTON ASSEMBLY FOR A DRUG DELIVERY DEVICE

CROSS REFERENCE TO RELATED APPLICATIONS

The present application is a divisional application of U.S. patent application Ser. No. 16/760,121, filed Apr. 29, 2020, which is the national stage entry of International Patent Application No. PCT/EP2018/079640, filed on Oct. 30, 2018, and claims priority to Application No. EP 18305967.4, filed on Jul. 17, 2018, and Application No. EP 17306510.3, filed on Nov. 2, 2017, the disclosures of which are incorporated herein by reference.

TECHNICAL FIELD

The present disclosure relates to a button and a button assembly for a drug delivery device, a drive mechanism containing such button or button assembly which is suitable for a drug delivery device, especially a pen type drug delivery device for selecting and dispensing a number of user variable doses of a medicament or an autoinjector. Further, the disclosure relates to such a drug delivery device.

BACKGROUND

The drive mechanism of a user settable drug delivery device often comprises a spring driven rotatable drive member, a rotatable driven member, a clutch for rotationally coupling the driven member and the drive member in a coupled state and allowing relative clockwise and/or anti-clockwise rotation between the driven member and the drive member in a decoupled state, and a (clutch) spring biasing the clutch into its coupled state and allowing relative axial movement between the drive member and the driven member into the decoupled state of the clutch against the bias of the spring. The clutch comprises teeth that are allowed to overridden by the drive member or the driven member in the de-coupled state of the clutch, e.g. during setting of a medicament dose, producing noise which is transmitted along the drug delivery device and which is perceived too loud.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Autoinjector drug delivery devices aim to make self-injection easier for patients. They often do not have the possibility to set the dose by the patient but are used to administer a pre-defined medicament dose. In many cases the administration of the medicament dose is triggered by moving a sleeve-like needle shield into a longitudinal direction (e.g. by the body surface of the patient), wherein the needle shield is initially in an extended position. In this case the needle shield acts like a dose button.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself.

Consequently, such disposable devices need not have a resettable dose setting mechanism.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing or trigger section connected to the one or the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly may be attached to one end of the cartridge assembly, then a dose may be set by the user, and then the set dose or the pre-defined dose is administered. Such removable needle assemblies may be threaded onto, or pushed (i.e., snapped) onto the pierceable seal end of the cartridge assembly. Alternatively, the needle is pre-assembled.

The dosing section or dose setting mechanism is typically the portion of the pen device that is used to set (select) a dose. During an injection, which is often initiated by actuating a button, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

In case of an autoinjector drug delivery device the needle shield may act as a button which causes the medicament contained within the cartridge to be injected as indicated above.

SUMMARY

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

With regard to all aspects of the specification explained below it may be noted that the term "drug delivery device" comprises devices which allow dose dialing of a user-defined dose of a medication and devices which eject a pre-defined dose of a medication such as autoinjectors.

Further, the drug delivery device has a proximal end which is opposite to a distal end. In many cases the button is accommodated at the proximal end. The distal end is often the end where the medication is ejected, preferably via a needle or another output element. The direction running from the proximal end to the distal end is referred to as the longitudinal or axial direction.

The numbering of the elements and components used in the following description is only used in order to distinguish the elements and components from each other. The numbering does not contain any content regarding the value or significance of the respective element or component.

In a first aspect the present disclosure provides a shock-resistant button assembly. Shock-resistant means with regard to this aspect that a shock impact at the button shall not lead to an operation of the button and injection or ejection of a medication.

In particular, the button assembly for a drug delivery device comprises a) a plate-like button body forming a touch surface and an axially elongated member connected to the plate-like button body for energy transmission to a driven element of the drug delivery device, or b) a sleeve-like button body forming a touch surface and a section that facilitates energy transmission to the driven element of the drug delivery device, and, for both alternatives a) and b) a support element, wherein the plate-like button body or the sleeve-like button body is movable into a longitudinal direction relative to the support element against the tension of a first resilient member retained by the support element and the plate-like button body or the sleeve-like button body, wherein the plate-like button body and/or the axially elongated member or the sleeve-like button body comprises a shock deactivation mechanism preventing movement of the plate-like button body or the sleeve-like button body relative to the support element or preventing transmission of a shock force to the driven element of the drug delivery device caused by the shock force acting at the plate-like button body or at the sleeve-like button body, wherein the shock force comprises at least one of a force component running transversal to the longitudinal direction of the button assembly and a force component running opposite to gravity.

In the embodiment a) the button assembly has a button in form of the plate-like button body forming the touch surface, wherein the button assembly may be accommodated at the proximal end of the drug delivery device or the drive mechanism.

In one embodiment the plate-like button body is movable into the longitudinal direction of the button assembly relative to the support element as long as it hits a stop surface at the support element.

In another embodiment the support element is or is formed by a dose selector or a housing, e.g. a proximal end of a housing, of the drug delivery device or drive mechanism. In one embodiment it comprises a recess within which the plate-like button body is accommodated. In one embodiment the plate-like button body of the button is accommodated such in the recess, that it is partially overlapped by the proximal end of the support element.

In another embodiment, the first resilient member, for example a compression spring (e.g. a coil spring), is supported on its distal end at a lateral surface of the support element and at its proximal end on the base or top surface of the plate-like button body, in particular a surface of the plate-like button body which is opposite the touch surface.

In one embodiment the axially elongated member has the form of a pin, stem, projection or a hollow cylinder and runs along the longitudinal direction of the button assembly, the drive mechanism or the drug delivery device. The axially elongated member may be formed integral with the plate-like button body or fixedly or is releasably attached to the plate-like button body.

According to the specification the shock deactivation mechanism prevents an injection or ejection of a medication as the plate-like button body of the button assembly does not move or—if it moves—the shock force is not transmitted to a driven element of the drug delivery device in case the drug delivery device with the button assembly observes an unintentional or accidental shock, for example when it falls down or hits a wall. The driven element may be a piston rod or a drive sleeve of the drug delivery device.

In one embodiment the deactivation mechanism is realized by a plate-like button body comprising a material composite with at least one first material component consisting of a first material and at least one second material component consisting of a second material different from the first material and having a higher elasticity and/or plasticity than the first material, wherein the second material forms at least partially a side surface, e.g. a circumferential part of the side surface, of the plate-like button body in a region opposite to a proximal end of the support element.

This embodiment works such that if the button assembly observes a shock force, for example with a force component transversal to the longitudinal direction of the button assembly, the proximal end of the support element and the deformable second material component of the plate-like button body become wedged together such that the plate-like button body cannot move into longitudinal direction. The proximal end of the support element, e.g. an edge of the support element, penetrates the deformable second material by deformation and thereby blocks the axial movement of the plate-like button body. Accordingly, medication dose ejection is prevented.

In one embodiment the plate-like button body is formed as a cylinder or disc (circular cylinder, elliptical cylinder) or a prism (cuboid, pentagonal, hexagonal etc). It may have a ring-like rim (i.e. the form corresponds to the base form of the plate-like button body) such that the cross section of the plate-like button body has a U-form. The base or the top side with the largest area of the plate-like button body forms the touch surface. The rim may project from the base or top side of the plate-like button body into longitudinal direction of the button assembly.

In one embodiment the first material component is a ring-like component. For example, the first material component forms an annular outer or outermost surface of the touch surface of the plate-like button body of the button assembly.

In one embodiment, for effective shock avoiding, the first material is as indicated above less deformable than the second material. The first material may, for example, consist of one or more compositions of the group comprising PC (polycarbonates), PBT (Polybutylene terephthalates) and POM (Polyoxymethylene). The second material is, for example, an injection moldable rubber mixture or thermoplastic elastomer (TPE), the second material may consist of, for example, one or more compositions of the group comprising styrenic block copolymers (TPE-s or TPS), thermoplastic olefins (TPE-o or TPO), elastomeric alloys (thermoplastic vulcanizates, TPE-v or TPV), thermoplastic polyurethanes (TPE-u or TPU), thermoplastic copolyester (TPE-E or TPC) and thermoplastic polyamides (TPE-A or TPA).

As the stiffness of the plate-like button body is not considerably effected, in one embodiment the area of the touch surface consisting of the first material is bigger than the area of the touch surface consisting of the second material, i.e. the largest proportion of the surface area of the touch surface is formed by one first material component.

Regarding the side surface (the area running perpendicular to the touch surface) of the plate-like button body in one embodiment the largest proportion of the side surface is formed by the second material component. In one embodiment, the proximal end of the support element overlaps the region of the side surface formed by the second material by more than 2 mm, preferably by more than 3 mm, for effective wedging in case of a shock event described above.

For effective force distribution a coupling plane between the first material component and the second material component is inclined with regard to the longitudinal direction.

In another embodiment the deactivation mechanism comprises an acceleration sensor.

In one embodiment the acceleration sensor comprises a seismic mass element (e.g. a heavy sphere, a cylinder or a polyeder made of a dense material, for example metal) which is accommodated within a recess of the plate-like button body or the axially elongated member, wherein a shock force with a force component running opposite to gravity causes a movement of the seismic mass element against the tension of a second resilient member (e.g. a compression spring, for example a coil spring) away from a resting position (seat) within the recess of the plate-like button body or the axially elongated member and parallel to the longitudinal direction of the button assembly.

In one embodiment the acceleration sensor takes two states. In first (normal) state the seismic mass element is pressed against its resting position (seat) by the resilient member. In a second state, in which it is forced by the shock force, the seismic mass element moves out of its resting position (away from its seat) by gravity and/or the shock force and against the tension of the resilient member. In the first state the force transmission of an axial (longitudinal) force from the plate-like button body to a driven element of the drug delivery device is allowed, whereas in the second state this force transmission is prevented by decoupling of the plate-like button body or of the axially elongated member from the driven element of the drug delivery device.

In one embodiment in the first state the seismic mass forces at least two bendable (deflectable) legs formed by the axially elongated member away from each other, whereas in the second state the two legs move towards each other. The deflective movement of the at least two legs has a component transversal to the longitudinal direction of the button assembly. In one embodiment the recess within the axially elongated member is formed by inner side of the at least two legs.

In one embodiment in the first state the plate-like button body and/or the axially elongated member are coupled to the driven element, for example by a projection at the outer surface of the axially elongated member in engagement with a proximal end surface of the driven element of the drug delivery device. In the second state the plate-like button body and/or the axially elongated member and the driven element are decoupled. For example, in the second state a projection at the outer surface of the axially elongated member may be disengaged from the proximal end surface of the driven element and axially movable relative to the driven element of the drug delivery device. Thereby the transmission of a shock force from the plate-like button body along the axial (longitudinal) direction to the driven element of the drug delivery device is prevented.

In the embodiment b) the button assembly has a button in form of the sleeve-like button body forming the touch surface, wherein the button assembly may be accommodated at the distal end of the drug delivery device or the drive mechanism. The embodiment b) may be suitable for an autoinjector and the sleeve-like button body is formed by the sleeve-like needle shield, wherein in an extended position the needle shield covers the needle and in an retracted position the needle shield exposes the needle. The sleeve-like button body (needle shield) is longitudinally movable between the extended position and the retracted position. The lateral distal surface of the sleeve-like button body (or needle shield) may form the touch surface which may be placed on the patient's skin surface and pressed into the direction of the skin in order to eject the pre-defined dose if the button assembly is integrated in an autoinjector.

In one embodiment the sleeve-like button body is movable into the longitudinal direction of the button assembly relative to the support element as long as it hits a stop surface at the support element.

In another embodiment the support element is or is formed by the housing, e.g. a distal end of the housing, of the drug delivery device or drive mechanism. In one embodiment it comprises a recess within which the sleeve-like button body is accommodated. In one embodiment the sleeve-like button body of the button is accommodated such in the recess, that it is partially overlapped by the distal end of the support element.

In another embodiment, the first resilient member, for example a compression spring (e.g. a coil spring), is supported on its proximal end at a lateral surface of the support element and at its distal end on an inner surface of the sleeve-like button body, in particular a surface of the sleeve-like button body which is opposite the touch surface.

According to the specification the shock deactivation mechanism prevents an injection or ejection of a medication as the sleeve-like button body of the button assembly does not move or—if it moves—the shock force is not transmitted to the driven element of the drug delivery device in case the drug delivery device with the button assembly observes an unintentional or accidental shock, for example when it falls down or hits a wall. The driven element may be a piston rod, a drive sleeve or a releasing element of the drug delivery device, wherein the releasing elements frees an, e.g. spring driven, drive mechanism leading to dose ejection.

In one embodiment the deactivation mechanism is realized by a sleeve-like button body comprising a material composite with at least one first material component consisting of the first material as indicated above and at least one second material component consisting of a second material as indicated above and different from the first material and having a higher elasticity and/or plasticity than the first material. The second material component may be formed as a circumferential section of the side surface of the sleeve-like button body, e.g. a ring-like section, for example a ring-like section with a larger outer diameter than the remaining side surface of the sleeve-like button body forming the first material component. The second material component may form a compressible or collapsible segment. In one embodiment the ring-like section is arranged in a region close to (i.e. in a short distance to) a distal end of the support element, referring to an extended position of the sleeve-like button body.

This embodiment works such that if the button assembly observes a shock force, for example with a force component transversal to the longitudinal direction of the button assembly, the distal end of the support element and the deformable or compressible second material component of the sleeve-like button body become wedged together such that the sleeve-like button body cannot move into longitudinal direction. The proximal end of the support element, e.g. an edge of the support element, penetrates the deformable second material by deformation and thereby blocks the axial movement of the sleeve-like button body. Accordingly, medication dose ejection is prevented.

As the stiffness of the sleeve-like button body is not considerably effected, in one embodiment the area of the side surface consisting of the first material is bigger than the area of the touch surface consisting of the second material, i.e. the largest proportion of the surface area of the touch surface is formed by one first material component. For example, the full surface area of the touch surface is formed by one first material component.

Regarding the side surface (the lateral area) of the sleeve-like button body in one embodiment the largest section of the side surface is formed by the first material component. In one embodiment, the distal end of the support element has a distance to the proximal end of the side surface formed by the second material component of less than 2 mm, preferably less than 1 mm, for effective wedging in case of a shock event described above.

In another embodiment the deactivation mechanism comprises an additional sleeve member (e.g. a hollow cylinder) accommodated within the sleeve-like button body. The additional sleeve member is referred to as the actuation sleeve in the following. The actuation sleeve comprises an actuation feature at its proximal end, for example a rim projecting from the outer surface of the actuation sleeve. The actuation feature may be engaged with the sleeve-like button body, for example within a corresponding recess in the inner surface of the sleeve-like button body. The actuation sleeve is movable into longitudinal direction against the force of a spring, rubber or elastomer component and may be axially guided by the sleeve-like button body. Initially, the actuation sleeve projects from the distal end of the sleeve-like button body. Further, the sleeve-like button body comprises a bendable segment (section) close to (e.g. within a short distance to) or overlapping with the support element. In case of an impact event by a shock force the actuation sleeve is forced to move relative to the sleeve-like button body in the longitudinal direction as it forms the distal-most end of the button assembly, pushes the actuation sleeve out of engagement with the bendable segment of the sleeve-like button body and thereby deforms the sleeve-like button body in the bendable segment such that the bendable segment and the distal end of the support element become wedged together thereby blocking the axial movement of the sleeve-like button body. The bendable segment forms the second material component and may consist of the second material as indicated above, whereas the remaining section of the sleeve-like button body forms the first material component and may consist of the first material as indicated above.

In a second aspect, the present disclosure provides a drive mechanism and a drug delivery device with a reduced operating loudness.

In particular, the button for a drug delivery device comprises a plate-like button body forming a touch surface, wherein the plate-like button body is coupled by an axial supporting member to a noise-generating interface of the drug delivery device and movable into a longitudinal direction of the drug delivery device, wherein the plate-like button body comprises a material composite with at least one third material component consisting of a third material and at least one fourth material component consisting of a fourth material different from the third material, wherein the at least one third material component and the at least one fourth material component are coupled via at least one coupling plane that is at least sectionwise slanted or perpendicular to the longitudinal direction.

The at least one coupling plane forms the interface between the third and the fourth material component. Accordingly, the at least one coupling plane couples the third material component and the fourth material component in a mechanical point of way and with regard to the sound transmission. At the at least one coupling plane the third material component and the fourth material component are permanently and/or releasable fixed together. The sound wave(s) received by the axial supporting member pass the at least one coupling plane on its way to the touch surface where the sound wave(s) couple to the air. In an embodiment the at least one coupling plane runs from the touch surface of the plate-like button body to the surface opposite to the touch surface of the plate-like button body, for example by a conical surface, a cylindrical surface or a polyhedral surface, wherein the respective surface may comprise some curvature.

In another embodiment there are at least two third material components and at least two coupling planes, namely between the one third material component and one fourth material component and the one fourth material component and another third material component.

On a more general level, the teaching of this aspect of the disclosure may be summarized in that by adding soft and/or high-density material to the button (i.e. the fourth material of the at least one fourth material component) between the surface that receives the noise and the touch surface of the button the natural frequency of the touch surface can be reduced and the ability of the button to damp vibrations caused by impacts of vibrating drive member or driven member of the drug delivery device is improved, in particular during dose dialing. Both of these effects will tend to reduce the loudness of the noise caused by the impact, and therefore reduce the operating loudness of the drug delivery device. As an underlying conceptual understanding thereof might be seen in the finding that, in circumstances, in a plate-like structure of the button a flat surface (i.e. the touch surface) may act, similar to a drumhead or membrane, as an amplification for noise transmitted to the structure of the button, e.g. noise caused by a projection of the button hitting a surface of a vibrating drive member and/or driven member.

In one embodiment, for effective noise damping, the third material may have a higher compressive strength than the fourth material and/or a higher inner sound damping than the fourth material and/or a lower viscosity than the fourth material. The third material may, for example, consist of one or more compositions of the group comprising PC (polycarbonates), PBT (Polybutylene terephthalates) and POM (Polyoxymethylene). The fourth material is, for example, an injection moldable rubber mixture or thermoplastic elastomer (TPE), the fourth material may consist of, for example, one or more compositions of the group comprising styrenic block copolymers (TPE-s or TPS), thermoplastic olefins (TPE-o or TPO), elastomeric alloys (thermoplastic vulcanizates, TPE-v or TPV), thermoplastic polyurethanes (TPE-u or TPU), thermoplastic copolyester (TPE-E or TPC) and thermoplastic polyamides (TPE-A or TPA).

As the noise damping is effected by leading the sound waves through the third and the fourth material, it is advantageous if the at least one coupling plane runs between the touch surface and the supporting member.

In another embodiment the supporting member may be formed by one third material component and/or the largest proportion of the surface area of the touch surface is formed by one third material component.

In one particular embodiment the button may comprise at least two third material components, wherein > one third material component is formed by a ring-like cladding element shaped to form the main part of the touch surface of the button,
>
> another third material component is formed by a central conical element and
>
> one fourth material component is formed by a conical ring-like element accommodated between the ring-like cladding element and the conical element. This embodiment is cost-effective in production.

In another embodiment the button may comprise a plurality of third material components and a plurality of fourth material components, wherein > one third material component is formed by a ring-like cladding element,
>
> another third material component is formed by a central cylindrical element,
>
> further third material components (different from the ring-like cladding element) are formed by a plurality of cross members running perpendicular to the longitudinal direction and connecting (and fixed at) the ring-like cladding element and the central cylindrical element and
>
> a plurality of fourth material components is formed by a plurality of polyhedral elements accommodated above and/or below the cross members between the cladding element and the central cylindrical element. The polyhedral elements may be realized for example by a trihedral pyramid (straight or inclined).

The above-mentioned ring-like, conical and cylindrical elements are understood not only as round elements but also as corresponding angular elements or partly angular elements. For example, the central cylindrical element may be realized as round cylindrical element or as polyhedral element, e.g. the element may have an octagonal cross section.

In this embodiment a first group of a plurality of cross members may form partly the touch surface of the button and a second group of the plurality of cross members may run offset from the first group of cross members and/or form at least partly a surface opposite to the touch surface of the button.

In another embodiment the button may comprise one third material component formed by a plate-like element and one fourth material component formed by a cap covering at least partly the plate-like element and forming at least partly the touch surface of the button. In this embodiment the whole surface of the plate-like element may be covered by the cap. The fourth material component then forms the touch surface of the button. This embodiment provides one example which allows upgrading of conventional drug delivery devices without any noise reduction.

In one embodiment the supporting member may be formed by a projection projecting from a central third material component into longitudinal direction. In this embodiment the projection is adapted to be supported at a support surface of the drive member and/or the driven member thereby forming the noise-generating interface.

The problem is also solved by a drive mechanism for a drug delivery device comprising the above-described button or button assembly.

In particular, the drive mechanism may comprise a spring driven rotatable drive member, a rotatable driven member, a clutch for rotationally coupling the driven member and the drive member in a coupled state and allowing relative clockwise and/or anti-clockwise rotation between the driven member and the drive member in a decoupled state, and a (clutch) spring biasing the clutch into its coupled state and allowing relative axial movement between the drive member and the driven member into the decoupled state of the clutch against the bias of the spring.

In one embodiment the clutch may comprise teeth that are allowed to overridden by the drive member or the driven member in the de-coupled state of the clutch, e.g. during dose setting, producing a vibrating movement of the drive member or the driven member in the decoupled state of the clutch.

The problem is further solved by a drug delivery device comprising the above-described button, the above-described button assembly or the above-described drive mechanism.

A clutch according to the disclosure is a component or feature suitable for connecting two component parts either by form fit (positive fit), e.g. with teeth suitable for engaging and disengaging each other, or by a non-positive (frictional) connection or a combination thereof.

Actuation of a clutch, i.e. the act of coupling or decoupling, may include a relative movement of clutch parts or clutch features, for example for disengaging clutch teeth, and/or may include a change in a force exerted on clutch parts or clutch features.

The crown teeth of the clutch are preferably provided as axially extending teeth located at the distal end face of one component part, e.g. the drive member, and the proximal end face of the other component part, e.g. the driven member. However, it is also possible to provide crown teeth in a recess or on a flange.

In a preferred embodiment of the disclosure, the drive mechanism further comprises a torsion spring which is directly or indirectly coupled to the drive member such that rotation of the drive member in a first rotational direction charges (strains) the spring and that rotation of the drive member in a second, opposite rotational direction discharges (releases) the spring. To reduce the torque necessary to overhaul the clutch during dose setting, while preventing unintended discharging of the torsion spring, the teeth may have a steeper ramped tooth angle in the second rotational direction and have a shallower ramped tooth angle in the first rotational direction. In addition or as an alternative, the teeth may have a higher friction coefficient in the second rotational direction and have a lower friction coefficient in the first rotational direction.

The drive member may be a separate component part which is rotationally constrained to a dose setting member, e.g. a number sleeve or a dose selector. The drive member may be rotatable and axially constrained, e.g. to a housing, or may be rotatable along a helical path. The driven member may be a tubular element located e.g. inside the number sleeve. On the other hand, the driven member may drive a further component part, for example a piston rod.

A drug delivery device for selecting and dispensing a number of user variable doses of a medicament preferably comprises a drive mechanism as defined above and further a housing, a dose setting member located within the housing and a piston rod engaging the driven member, wherein the drive member is operatively interposed between the driven member and the dose setting member. In this embodiment the drive member may act as a clutch element for coupling and decoupling the driven member and the dose setting member, e.g. to allow relative rotation during dose setting (or dose correcting) and to prevent relative rotation during dose dispensing.

The drug delivery device may further comprise a second clutch for rotationally coupling and decoupling the driven member and the housing. Preferably, the driven member is axially displaceable relative to the housing between a first position in which the second clutch rotationally couples the driven member and the housing and a second position in which the second clutch rotationally decouples the driven member from the housing. In other words, the drug delivery device may be switched between a dose setting (or correcting) state in which rotation of the driven member is prevented and a dose dispensing state in which rotation of the driven member is allowed by axial movement of the driven member. In this respect, a button may be provided acting directly or indirectly on the driven member for axial displacement, e.g. against the bias of the clutch spring.

When switching between the dose setting (or correcting) state and the dose dispensing state it is desirable to avoid uncontrolled movement of the driven member, especially in embodiments where the driven member is coupled to a piston rod or the like effecting dose dispensing. Such uncontrolled movement of the driven member could result in amending the set dose prior to dispensing, i.e. underdosage or overdosage. To avoid uncontrolled movement of the driven member the teeth of the clutch are preferably in its coupled state when the driven member and the housing are decoupled by the second clutch. Further, the driven member and the housing are preferably coupled by the second clutch when the teeth of the clutch are in its decoupled state. In other words, the driven member is permanently coupled to at least one of the drive member and the housing.

All above embodiments may be combined, in particular the different embodiments of the first aspect or the embodiments of the first aspect and the second aspect.

Further, the drug delivery device may comprise a cartridge containing a medicament. The term "medicament" or "medicament formulation", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin;

Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(02)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by A and K. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Non-limiting, exemplary embodiments of the aforementioned working principles will now be described with reference to the accompanying drawings, in which.

DETAILED DESCRIPTION

As indicated above the numbering of the elements and components used in the following description is only used in order to distinguish the elements and components from each other. The numbering does not contain any content regarding the value or significance of the respective element or component.

Figure 1:
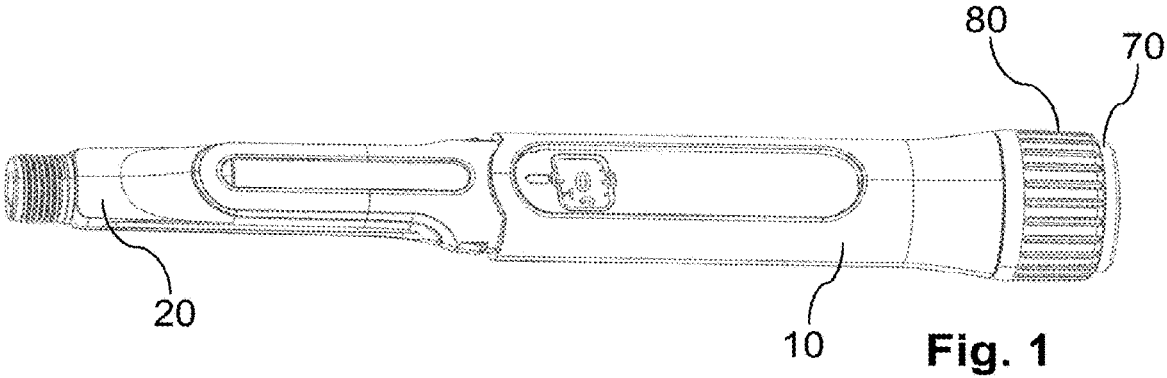
FIG. 1 shows a top view of a drug delivery device.
Figure 2:
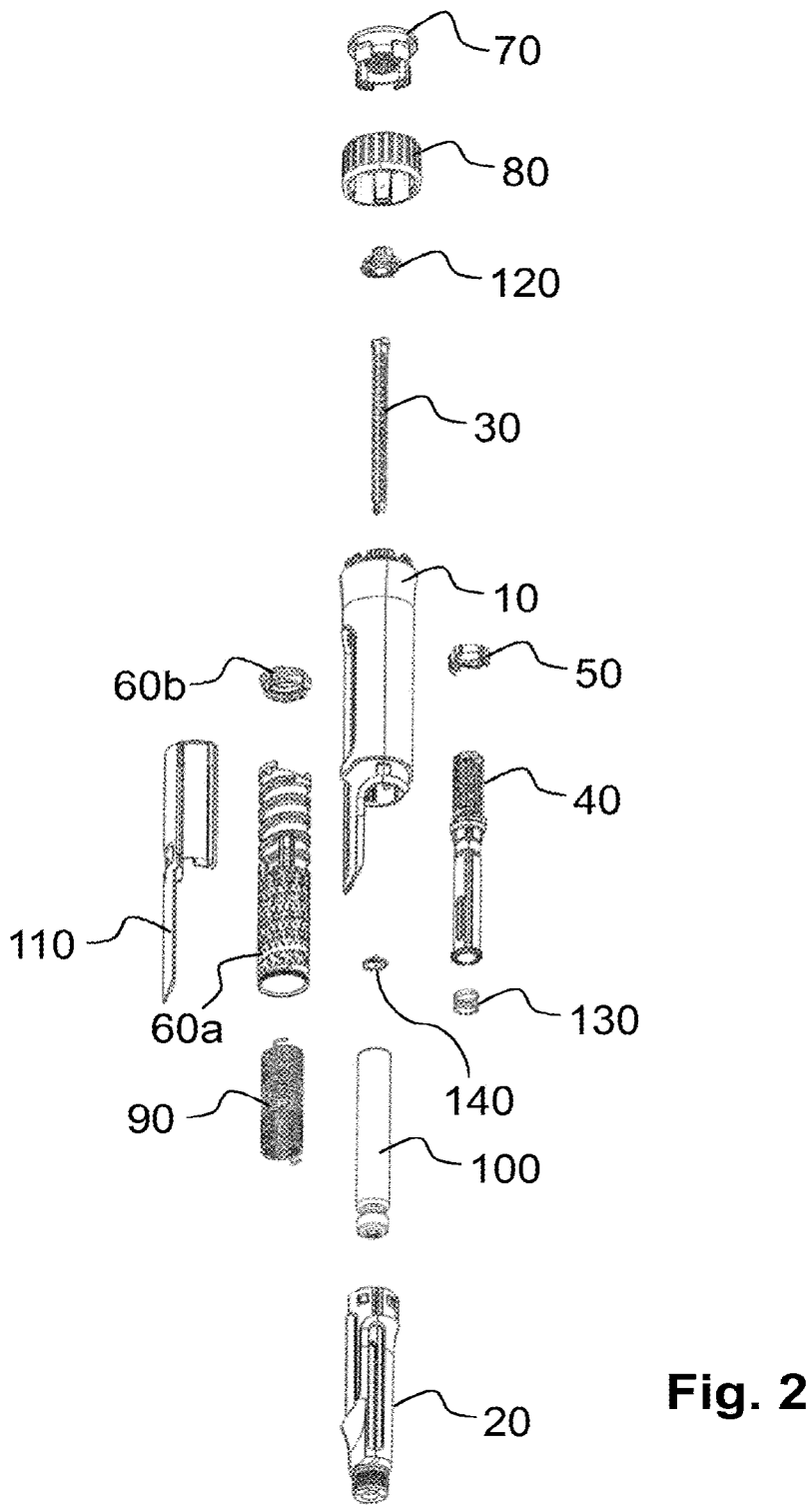
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

As will be explained in more detail below, the clutch plate 120 is a spring driven rotatable drive member driving the drive sleeve 40 during dose dispensing to rotate relative to the housing 10 to thereby advance piston rod 30. The clutch plate 120 is in turn driven by the number sleeve 60 to which it is rotationally constrained which is attached to one end of the torsion spring 90. On the other hand, although driving the piston rod 30 during dose dispensing, the drive sleeve may be regarded as a driven member because it is driven by the clutch plate 120 (and the number sleeve 60 and the torsion spring 90) during dose dispensing.

The housing 10 or body is a generally tubular element having a proximal end with an enlarged diameter. The housing 10 provides location for the liquid medication cartridge 100 and cartridge holder 20, windows for viewing the dose number on the number sleeve 60 and the gauge element 110, and a feature on its external surface, e.g. a circumferential groove, to axially retain the dose selector 80. An insert 12 comprises an inner thread engaging the piston rod 30. The housing 10 further has at least one internal, axially orientated slot or the like for axially guiding the gauge element 110. In the embodiment shown in the FIG. 2, the distal end is provided with an axially extending strip partly overlapping cartridge holder 20. FIG. 2 depicts the housing 10 as a single housing component. However, the housing 10 could comprise two or more housing components which may be permanently attached to each other during assembly of the device. The drive spring 90 is attached with one end to the housing 10.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track at the piston rod 30 and a corresponding protrusion or spline of the drive sleeve 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130. At least one longitudinal spline of the drive sleeve 40 engages a corresponding track of the lead screw 30.

The clutch interface between the drive sleeve 40 and the clutch plate 120 comprises a ring of ratchet (crown) teeth 41 located on the proximal end face of the drive sleeve 40 and a ring of corresponding ratchet (crown) teeth 121 located on the distal end face of the clutch plate 120.

A splined tooth interface 11, 42 with the housing 10 prevents rotation of the drive sleeve 40 during dose setting. This interface comprises a ring of radially extending outer teeth 42 at the distal end of drive sleeve 40 and corresponding radially extending inner teeth 11 of the housing component 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialling, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

The drive sleeve 40 has a threaded section providing a helical track for the nut 50, i.e. a thread. In addition, a last dose abutment or stop is provided which may be the end of the thread track or preferably a rotational hard stop for interaction with a corresponding last dose stop of nut 50, thus limiting movement of the nut 50 on the drive sleeve thread.

A further interface of the drive sleeve 40 comprises the ring of ratchet teeth 41 located at the proximal end face of drive sleeve 40 and the ring of corresponding ratchet teeth 121 on the clutch plate 120.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialling only. As an alternative, the nut 50 may be splined to the drive sleeve 40 and threaded to the number sleeve 60. A last dose stop is provided on nut 50 engaging a stop of drive sleeve 40 when a dose is set corresponding to the remaining dispensable amount of medicament in the cartridge 100.

The dose indicator or number sleeve 60 is a tubular element. The number sleeve 60 is rotated during dose setting (via dose selector 80) and dose correction and during dose dispensing by torsion spring 90. The number sleeve 60 is axially constrained to the housing 10, e.g. by snap engagement of a bead on an inner housing surface with a groove on an outer number sleeve surface, while being free to rotate relative to the housing 10. The drive spring 90 is attached with one end to the number sleeve 60. Further, the number sleeve 60 is in threaded engagement with the gauge element 110 such that rotation of the number sleeve causes axial displacement of the gauge element 110. Together with gauge element 110 the number sleeve 60 defines a zero position ('at rest') and a maximum dose position. Thus, the number sleeve 60 may be seen as a dose setting member. The number sleeve 60 may comprise a number sleeve lower 60a which is rigidly fixed to a number sleeve upper 60b during assembly, e.g. by snap engagement, to form the number sleeve 60.

Clutch features which have the form of a ring of splines are provided inwardly directed on number sleeve upper 60b for engagement with splines of the button 70 during dose setting and dose correction. A clicker arm is provided on the outer surface of number sleeve 60 which interacts with the drive sleeve 40 and the gauge member 110 for generating a feedback signal.

In addition, the number sleeve lower 60a is rotationally constrained to the nut 50 and to the clutch plate 120 via a splined interface comprising at least one longitudinal spline. Further, number sleeve lower 60a comprises an interface for attachment of the torsion spring 90.

Figure 3:
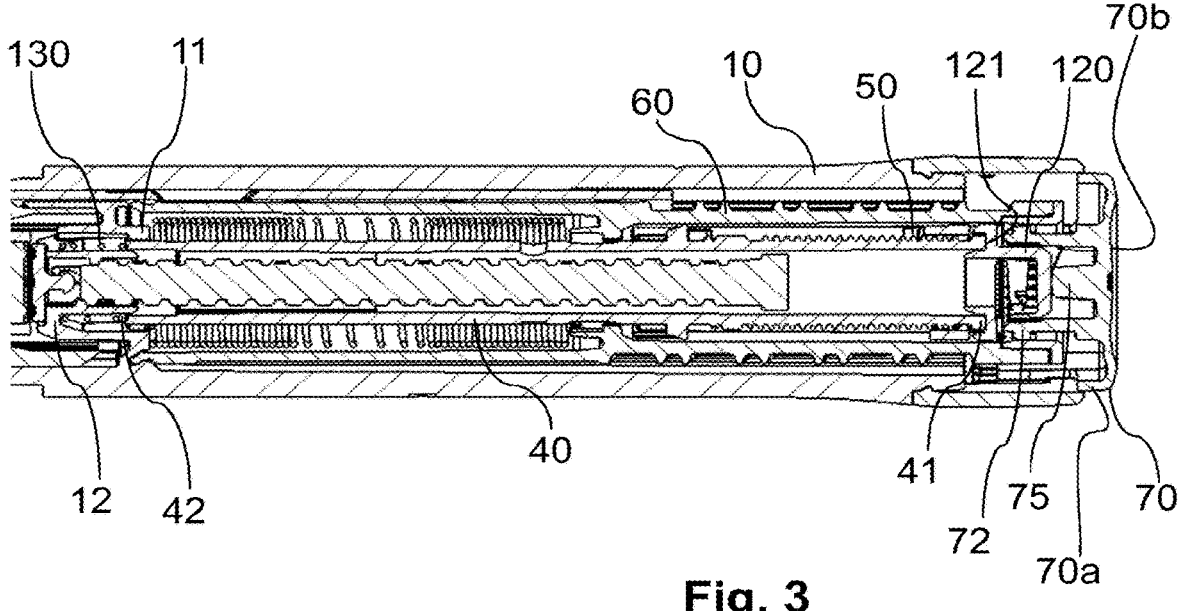
FIG. 3 shows a sectional view of the proximal end of the device of FIG. 1.

The button 70 forms the proximal end of the device. It may be beneficial if the button 70 is permanently splined to the dose selector 80 by a respective sleeve section 70a fixed at the rim of a plate-like button body projecting into distal direction forming the touch surface 70b. A central stem 72 may extend distally from the proximal face of the plate-like button body as it is shown in FIG. 3. The stem is provided with a flange carrying the splines for engagement with splines of the number sleeve upper 60b. Thus, it is also splined via splines to the number sleeve upper 60b when the button 70 is not pressed, but this spline interface is disconnected when the button 70 is pressed. The button 70 may have a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. The button further comprises a central projection 75 projecting from the distal face of the plate-like button body. The central projection 75 forms a central point support at the proximal surface of the clutch plate 120. During dose dispense the button 70 transmits the axial pressing force of the user via this central projection 75 into distal direction to the clutch plate 120 against the bias of the clutch spring 130.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the FIG. 2, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via the ratchet clutch interface 41, 121. The ratchet clutch 41, 121 provides a detented position between the number sleeve 60 and drive sleeve 40 corresponding to each dose unit, and engages different ramped tooth angles during clockwise and anti-clockwise relative rotation. A clicker arm may be provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth 42 are engaged with teeth 11 of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

The drug delivery device further may provide a visual feedback feature in addition to the discrete dose number display typical on devices of this type. The distal end of the gauge element 110 creates a sliding scale through the window in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth 42 with teeth 11 of the housing 10. Relative rotation must therefore occur between the clutch plate 120 and drive sleeve 40 via the ratchet clutch interface 41, 121.

The user torque required to rotate the dose selector 80 is a sum of the torque required to wind up the torsion spring 90, and the torque required to overhaul the ratchet clutch interface 41, 121. The clutch spring 130 is designed to provide an axial force to the ratchet clutch interface 41, 121 and to bias the clutch plate 120 onto the drive sleeve 40. This axial load acts to maintain the teeth engagement of the clutch plate 120 and drive sleeve 40. The torque required to overhaul the ratchet clutch 41, 121 in the dose set direction is a function of the axial load applied by the clutch spring 130, the clockwise ramp angle of the ratchet teeth 41, 121, the friction coefficient between the mating surfaces and the mean radius of the ratchet clutch interface 41, 121. When overrunning the ratchet teeth 41 of the drive sleeve 40 the clutch plate 120 vibrates back and forth into axial direction thereby hitting the central projection 75 of the button 70 and producing a noise which couples to the surrounding air by the touch surface 70*b* operating similarly to an air drum. Measures to reduce this noise are described in detail below referring to FIGS. 4 to 9.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet clutch interface 41, 121 between the clutch plate 120 and the drive sleeve 40. The torque necessary to overhaul the ratchet clutch 41, 121 in the anti-clockwise direction is a function of the axial load applied by the clutch spring 130, the anti-clockwise ramp angle of the ratchet 41, 121, the friction coefficient between the mating surfaces and the mean radius of the ratchet clutch features 41, 121. The torque necessary to overhaul the ratchet clutch 41, 121 must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet clutch interface 41, 121 between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet clutch 41, 121 in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect (correct) any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 41, 121 between the clutch plate 120 and drive sleeve 40 in the anti-clockwise direction. When the ratchet clutch 41, 121 is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed using the touch surface 70b, splines between the button 70 and number sleeve 60 are disengaged, rotationally disconnecting the button 70 and dose selector 80 from the delivery mechanism, i.e. from number sleeve 60, gauge element 110 and torsion spring 90.

Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface 41, 121 between the drive sleeve 40 and number sleeve 60, preventing relative rotation between the drive sleeve 40 and number sleeve 60 during dispense. The splined tooth interface 11, 42 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense may be provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth 11, 42 between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

Figure 4:
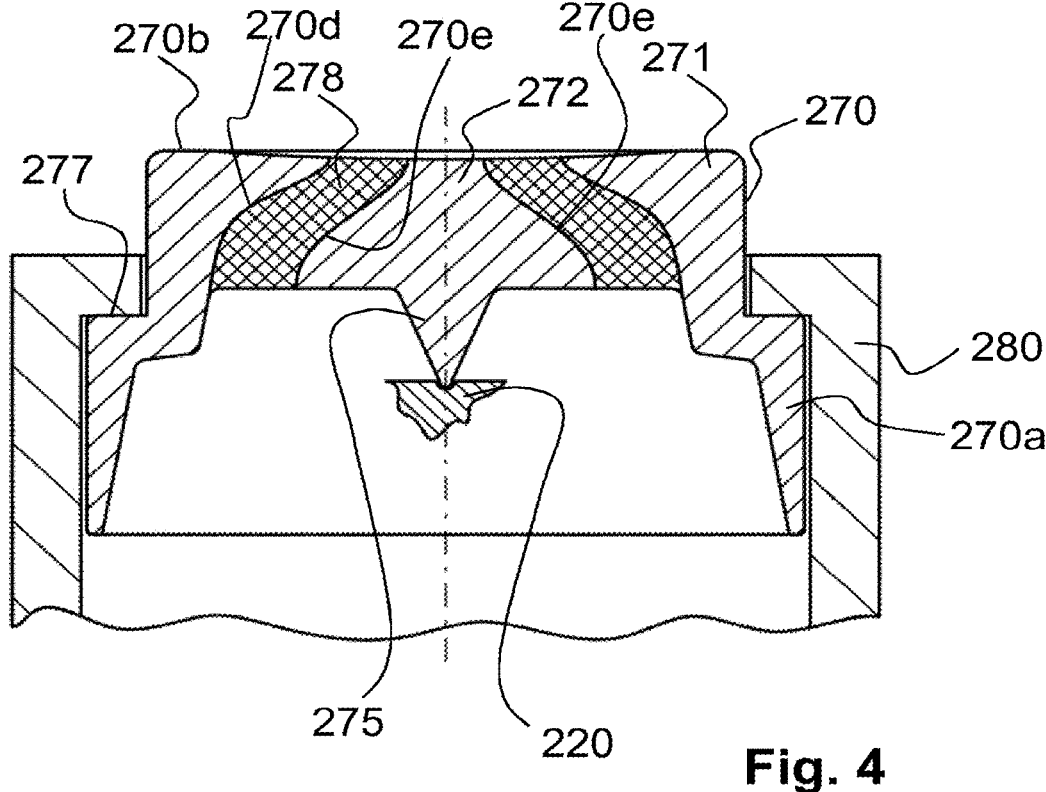
FIG. 4 shows a sectional view of a first embodiment of a button.
Figure 5:
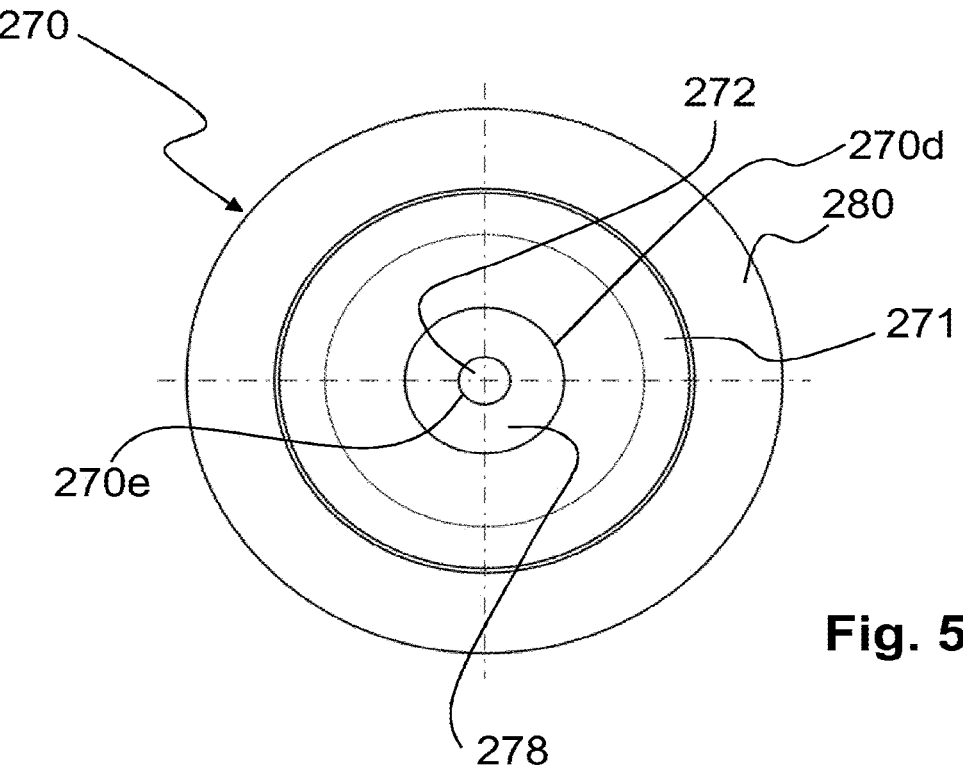
FIG. 5 shows a top view of the embodiment of FIG. 4.

FIGS. 4 and 5 show an embodiment of a button 270. This button comprises no central stem as the button 70 shown in FIG. 3 (see central stem 72) but may be realized with such a stem, if necessary, based on the design of the corresponding drug delivery device. Additionally, the sleeve section 270a fixed at the rim of the plate-like button body has a greater length in axial direction than in the embodiment shown in FIG. 3 and is permanently splined with the dose selector 280 (or, alternatively, with the housing) of the drug delivery device. Dependent on the design of the drug delivery device the sleeve section may shorter and/or be constructed as shown in FIG. 3 (sleeve section 70a) as well. The ring-like cladding element 271 comprises at its proximal side a flange-like surface 277 which abuts to a respective surface provided by the dose selector 280 in a proximal end position of the button 270.

The button 270 shown in FIG. 4 comprises a plate-like button body forming a touch surface 270b which is pressed by the user in order to administrate the medicament as described above. The plate-like button body comprises a ring-like cladding element 271, a central conical element 272 and a conical ring-like element 278. The conical ring-like element 278 is situated in between the ring-like cladding element 271 and the central conical element 272. The central conical element 272 comprises a projection 275 which forms the axial supporting member and which projects from the distal surface of this element opposite to the touch surface 270b. The projection 275 transmits the axial force provided by the user in case the user presses the touch surface 270b into distal direction or receives vibrational hits provided by the clutch plate 220 causing noise and transmits the noise via the projection 275 to the touch surface 270b.

The ring-like cladding element 271 and the central conical element 272 form a third material component (see above comment regarding the numbering) of the button 270 whereas the conical ring-like element 278 forms a fourth material component of the body of the button 270. The third material component consists of a third material and the fourth material component consists of a fourth material different from the third material, wherein the third material has a higher compressive strength than the fourth material and/or a higher inner sound damping than the fourth material and/or a lower viscosity than the fourth material. The third material consist of, for example PC, PBT or POM, and the fourth material consists of, for example, one of the above mentioned thermoplastic elastomers.

The ring-like cladding element 271 and the conical ring-like element 278 are coupled via a first coupling plane 270d that is sectionwise slanted with regard to the axial (longitudinal) direction of the noise. As indicated above the propagation direction of the noise is mainly axially and into proximal direction. Accordingly, the conical ring-like element 278 is coupled with central conical element 272 with a second coupling plane 270e that is sectionwise slanted with regard to the propagation direction of the noise as well. The first and the second coupling plane 270d, e sectionwise form a conical face with regard to the longitudinal direction and comprise some curved sections.

As one can derive from FIG. 5, the ring-like cladding element 271 forms the biggest ring-like area at the touch surface 270b compared with the area of the conical ring-like element 278 and the conical element 272.

The noise produced by hits of the surface of the clutch plate 220 to the distal end of the projection are damped by passing the fourth material of the fourth material component (ring-like element 278) thereby reducing the noise considerably.

The embodiments of a button 370, 470 shown in FIGS. 6 to 9 differ from the embodiment of FIGS. 4 and 5 in the shape of the third material component and the fourth material component. The other elements correspond to the respective elements of the embodiment shown in FIGS. 4 and 5 comprising the same tens and unit places (if applicable with letter).

Figures 6, 7:
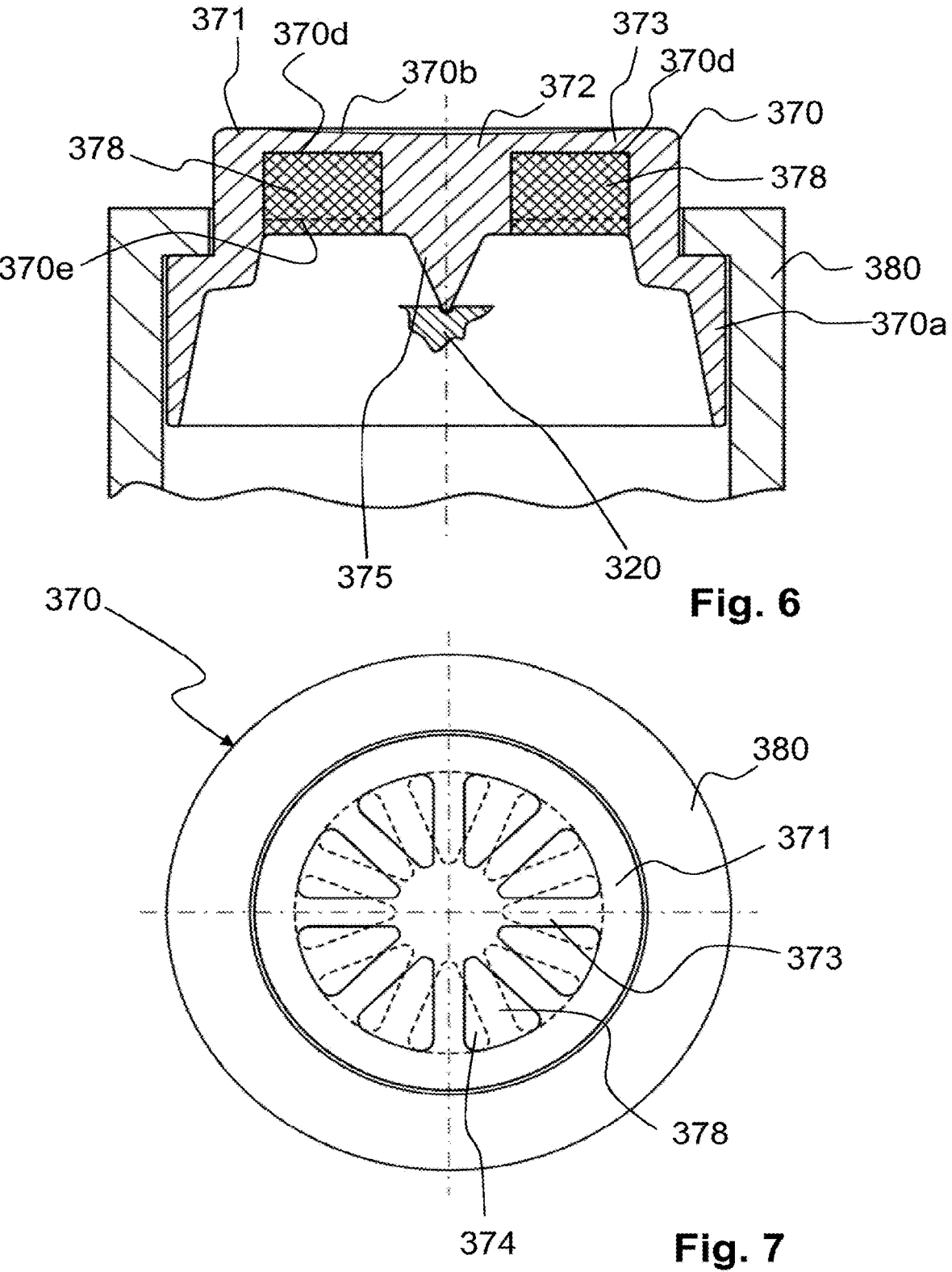
FIG. 6 shows a sectional view of a second embodiment of a button.
FIG. 7 shows a top view of the embodiment of FIG. 6.

The third material component of the embodiment of FIGS. 6 and 7 comprises a ring-like cladding element 371, a central cylindrical element 372 and a plurality of cross members 373, 374 running perpendicular to the axial direction and connecting the ring-like cladding element 371 and the central cylindrical element 372. A first group of a plurality of cross members 373 form the touch surface 370b of the button 370 and run radially (e.g. similar to spoke-like struts). A second group of a plurality of cross members 374 form the surface opposite to the touch surface 370b. In between the first group of a plurality of cross members 373 and the second group of a plurality of cross members 374 a plurality of polyhedral elements 378, e.g. of trihedral elements, is accommodated, wherein the polyhedral elements 378 fill the space between the central cylindrical element 372 and the ring-like cladding element 371. The first group of a plurality of cross members 373 and the second group of a plurality of cross members 374 run offset from each other as shown in FIG. 7.

Figures 8, 9:
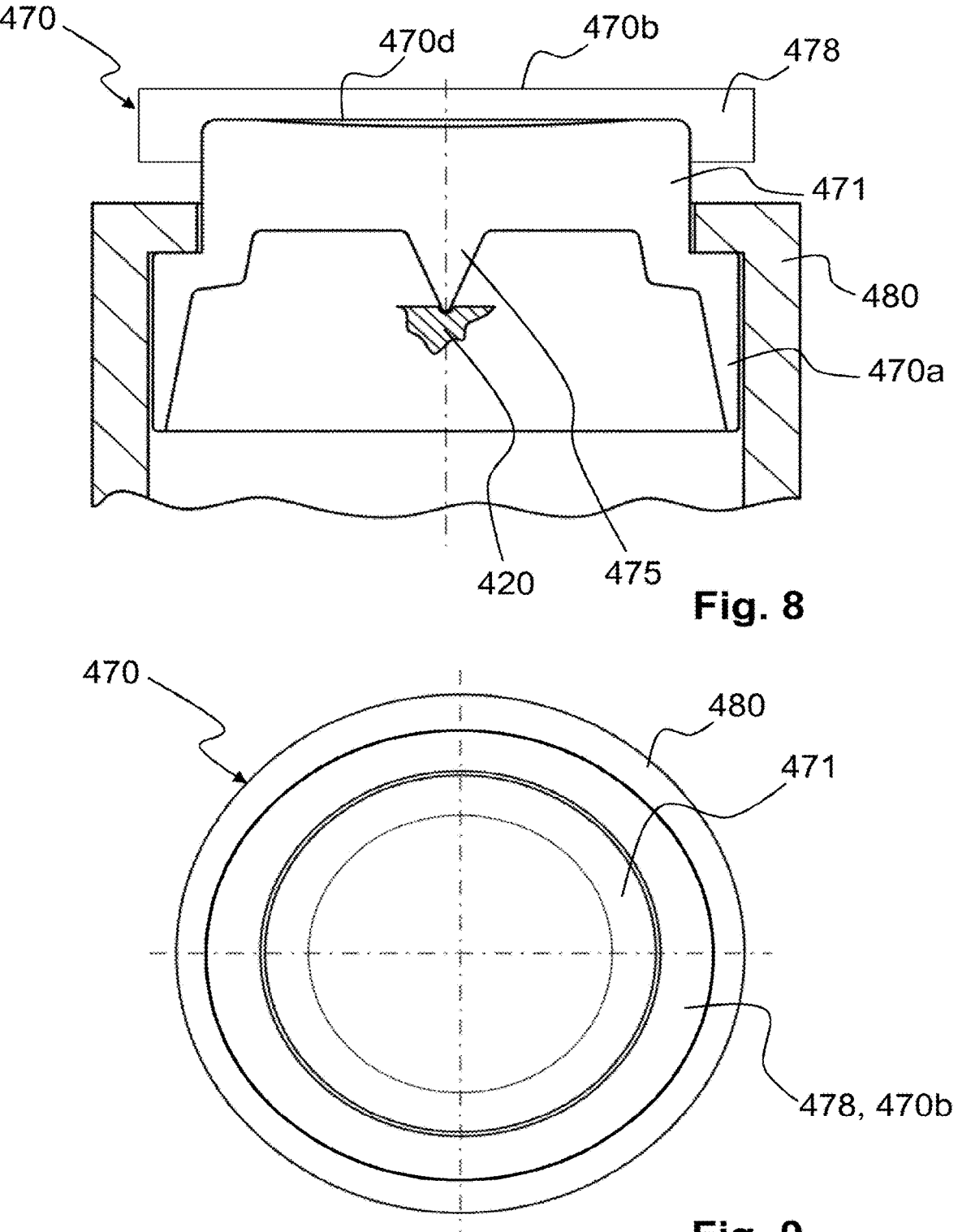
FIG. 8 shows a sectional view of a third embodiment of a button.
FIG. 9 shows a top view of the embodiment of FIG. 8.

The embodiment of a button 470 shown in FIGS. 8 and 9 comprises a plate-like element 471 forming the third material component which is covered on its entire surface by a cap 478 forming the fourth material component and the touch surface 470b. The proximal surface of the plate-like element forms the coupling plane 470d.

The coupling planes 370d, 370e, and 470d of the embodiments shown in FIGS. 6 to 9 run perpendicular to the axial direction which is shown in FIGS. 4, 6, 8 by a dotdashed line.

The third material components 371, 372, 373 and 374 consist of the third material and the fourth material components 378, 478 consist of the fourth material. As indicated above, the third material component may consist of PC, PBT or POM, for example, and the fourth material component may consist of one of the above mentioned thermoplastic elastomers. The fourth material component provides the noise damping as explained in detail above with regard to the embodiment of FIGS. 4 and 5.

Figures 10, 11, 12:
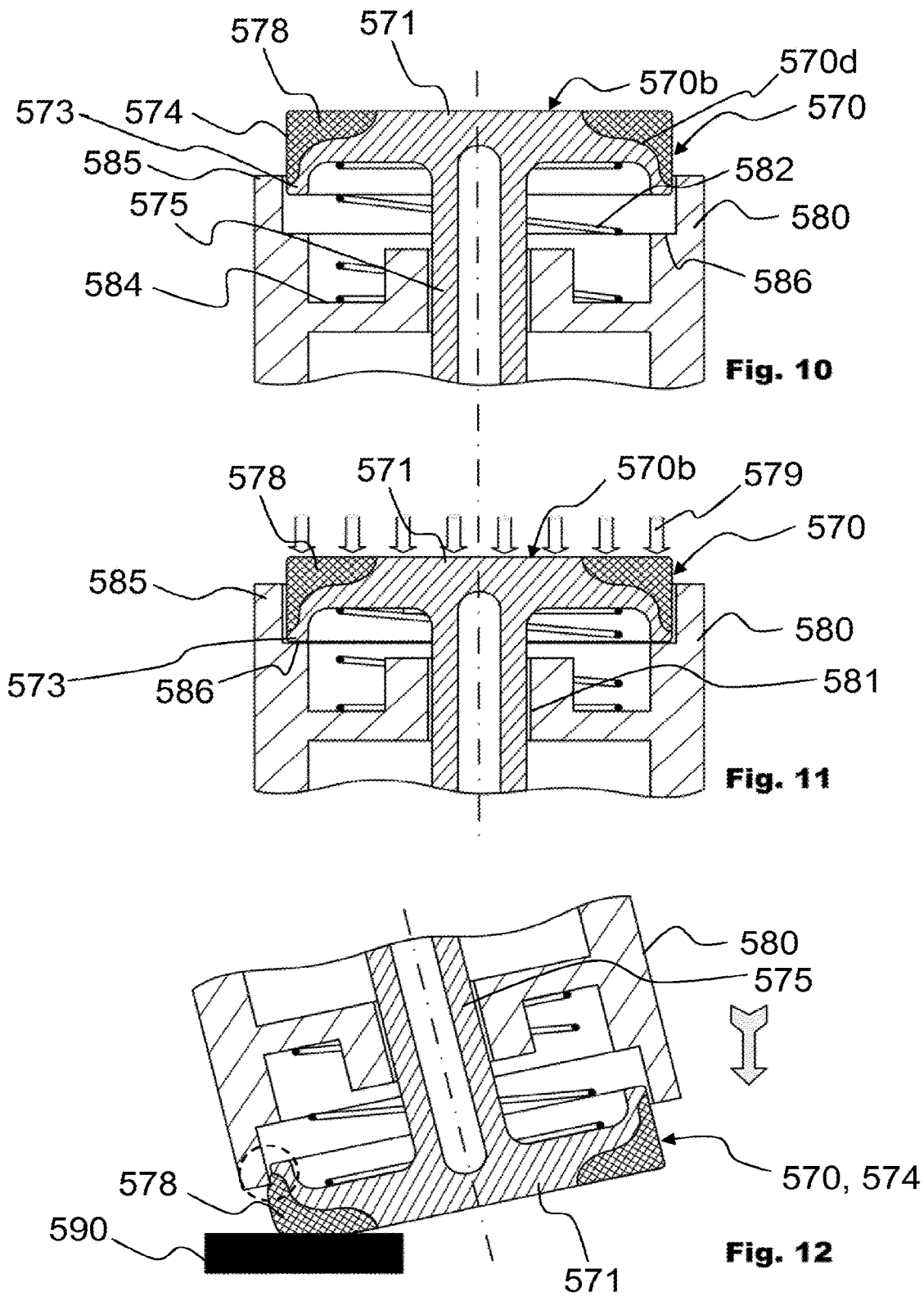
FIG. 10 shows a sectional view of a first embodiment of a button assembly.
FIG. 11 shows the view of FIG. 10 during activation of dose injection.
FIG. 12 shows the view of FIG. 10 in case a shock force acting at the button.

FIGS. 10 to 12 show an embodiment of a button assembly accommodated at the proximal end of a drug delivery device. This button assembly comprises a plate-like button body 570 forming the button and its touch surface 570b at the proximal end face. Further, a central stem or projection 575 forming an axially elongated member is provided at the distal end face of the plate-like button body 570 for force transmission to a driven element (not shown) of the drug delivery device (e.g. a force provided by the user when the button is pressed in order to inject a user-defined or predefined dose). In one embodiment the central stem 575 is a hollow cylinder. The central stem 575 is fixedly or removably attached to the plate-like button body 570 or is (as shown in FIGS. 10 to 12) formed integrally with the plate-like button body 570.

Additionally, the button assembly comprises a dose selector 580 (or, alternatively, a proximal end of the housing) forming a support element. The central stem of the button is accommodated within a respective through hole 581 of the dose selector 580. Further a resilient member in form of a spring 582 (e.g. a compression spring, for example a coil spring) is provided, wherein the plate-like button body is biased by the spring 582 against an axial movement into distal direction. The spring 582 is supported by the distal end face of the plate-like button body 570 and a proximal inner wall surface 584 of the dose selector 580.

The plate-like button body 570 forming the touch surface 570b of the button comprises further an outer rim 573 at its distal end face projecting from this distal end face in distal direction. Further, the plate-like button body 570 comprises a first material component forming a central section 571 of the plate-like button body 570 and a second material component forming a ring-like outer section 578 of the plate-like button body 570. The ring-like outer section 578 comprises an approximately triangular cross section as shown in FIGS. 10 to 12. By the triangular cross section it is ascertained that the ring-like outer section 578 forms the largest section of the side surface 574 of the plate-like button body 570 and the outermost annular section of the touch surface 570*b*. In particular, the section of the side surface 574 is formed by the ring-like outer section 578 which is opposite to a proximal end section 585 of the dose selector 580.

The plate-like button body 570 shown in FIG. 11 is pressed by the user (see arrows 579) in order to administrate the medicament as described above. The axial or longitudinal force provided by the user for dose administration acts against the tension of the spring 582 and moves the plate-like button body 570 axially into distal direction. The axial force is transmitted by stem 575 to a driven element (not shown) of the dose delivery device. The plate-like button body 570 moves until its rim 573 hits a stop surface 586 provided at the dose selector 580 and formed by a step surface in its inner wall.

The central section 571 consists of a first material and the ring-like outer section 578 consists of a second material different from the first material, wherein the second material has a higher elasticity and/or plasticity than the first material. The first material consist of, for example PC, PBT or POM, and the second material consists of, for example, one of the above mentioned thermoplastic elastomers.

The ring-like outer section 578 and the central section 571 are coupled via a coupling plane 570*d* that is sectionwise slanted with regard to the axial (longitudinal) direction (see dot and dash line) of the button assembly or drug delivery device.

As one can derive from FIGS. 10 to 12, the central section 571 forms a circular area at the touch surface 570*b* that is bigger than the annular area of the ring-like outer section 578. This ensures that the force provided by the user is properly transmitted by the first material of the central section 571 to the drug delivery device via stem 575. The material of the central section 571 has a low elasticity and/or plasticity.

The material of the ring-like outer section 578 has a higher elasticity and/or plasticity than the central section 571 and provides a shock deactivation mechanism. The shock deactivation mechanism adapted such that in case of a shock event as shown in FIG. 12, where a ridge of the plate-like button body 570 obliquely hits the floor (or wall) 590 after a fall of the drug delivery device (and the button assembly accordingly) under gravity, there is an elastic and/or plastic deformation of the ring-like outer section 578. Additionally, this deformation caused by a force comprising a component transversal to the longitudinal direction leads to wedging together of the plate-like button body and the distal end of the dose selector 580 (see area marked with dashed-line circle). Thereby, axial movement of the plate-like button body 570 and the attached stem 575 relative to the dose selector 580 is prevented. Hence, the shock force is not transmitted to the driven element of the drug delivery device. Accordingly, in case of such shock event, a medication dose is not administered.

In another embodiment shown in FIGS. 13 to 15 there is another shock deactivation mechanism described below in detail. However, it may be combined with the deactivation mechanism described and shown in FIGS. 10 to 12.

The reference number with the same last two numbers have the same function as in the embodiment of FIGS. 10 to

12. With regard to the embodiment of FIGS. 13 to 15 the first number of the reference number is 6 instead of 5 of the embodiment of FIGS. 10 to 12.

Figures 13, 14, 15:
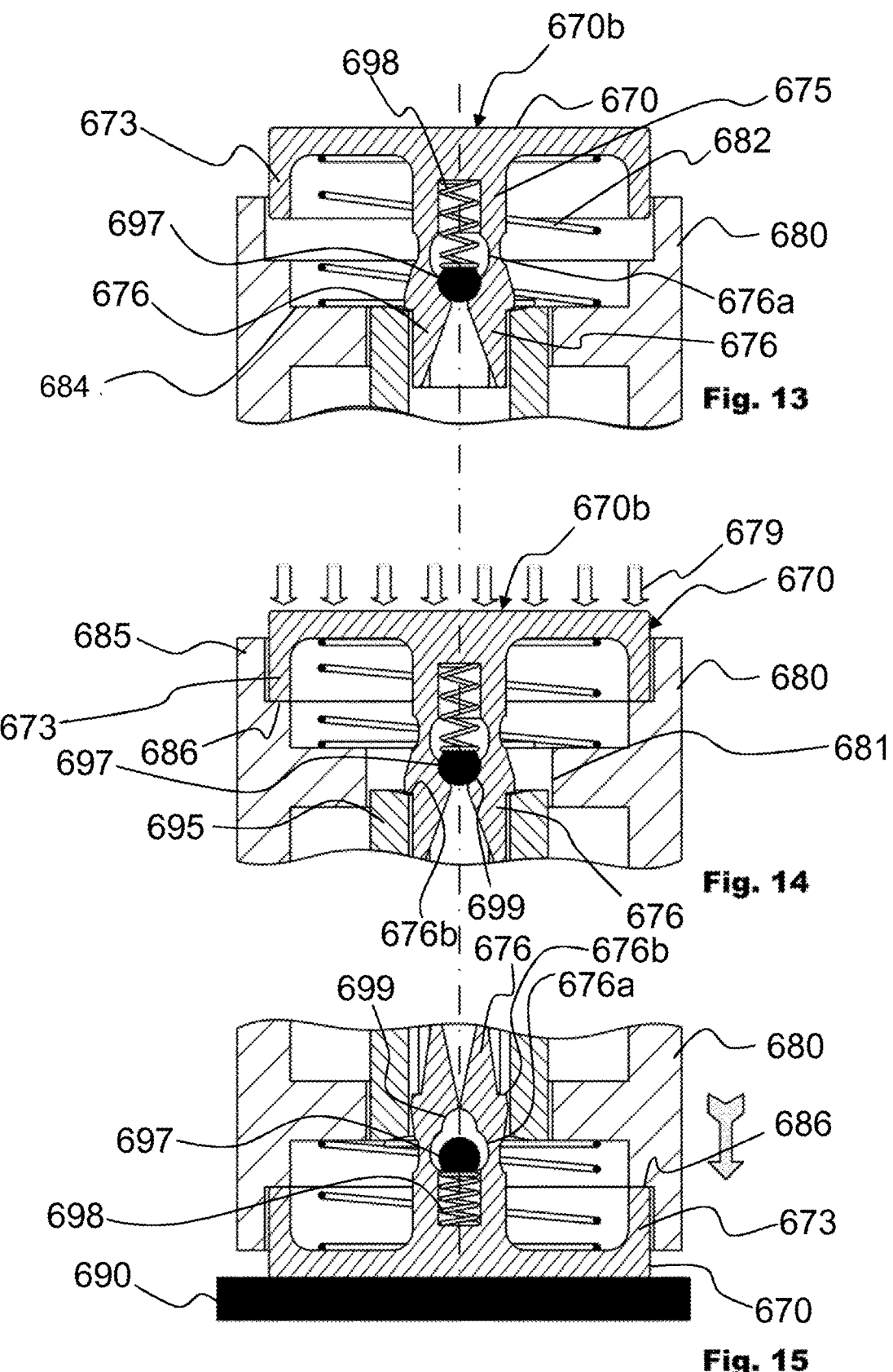
FIG. 13 shows a sectional view of a second embodiment of a button assembly.
FIG. 14 shows the view of FIG. 13 during activation of dose injection.
FIG. 15 shows the view of FIG. 13 in case a shock force acting at the button

The embodiment of FIGS. 13 to 15 comprises a stem (projection) 675 for force transmission of an axial force provided by the user to the elements of the drug delivery device for administration of as medication dose, in particular to a driven element 695 formed as a hollow cylinder. This stem 675 is formed integrally with the plate-like button body 670 or is attached to it at its distal surface. At its distal end the stem 675 is divided into two legs 676 separated by a recess 676*a*. The legs 676 are bendable in a direction transversal to the longitudinal direction of the button assembly (see dot and dashed line) such that in a first state the legs 676 are forced apart such that an outer projection 676*b* of each leg 676 abuts to a proximal end face of a driven element 695 of the drug delivery device (for example the clutch plate 120 or the drive sleeve 40 shown in FIGS. 2 and 3). This state is shown in FIGS. 13 and 14.

A second state is shown in FIG. 15. In this state the legs 676 are moved towards each other such that they may even become in contact with each other. By the movement towards each other the overall outer diameter across the legs 676 at the outer projections 676*b* becomes smaller such that the outer projections 676*b* of the legs 676 are not engaged with the proximal end face of the driven element 695 of the drug delivery device. Instead, the legs 676 are moved within a central recess 696 of the driven element 695 of the drug delivery device relative to the driven element 695. Hence, there is no transmission of an axial force from the plate-like button body 670 to the driven element 695 in the second state.

The first state and the second state of the legs 676 of the stem are caused by a deactivation mechanism comprising an acceleration sensor provided within the recess 676*a* of the stem 675. The acceleration sensor comprises a seismic mass formed by a heavy (e.g. metal) sphere 697 and a compression spring 698 as a resilient member formed by a coil spring. The compression spring 698 is provided with in the recess 676*a* of the stem 675 such that it presses the metal sphere 697 against a seat 699 (i.e. its resting position) within the recess 676*a* formed by the two legs 676 at the distal and of the recess 676*a*. The compression spring 698 is supported at its distal end at the metal sphere 697 and at its proximal end at the proximal end face of the recess 676*a*.

The first (normal) state of the legs 676 explained above is realized if the metal sphere 697 is pressed against its seat 699 (resting position) by the compression spring 698 (see FIGS. 13, 14) and thereby forcing the two legs 676 apart. The drug delivery device with the button assembly can be used in a conventional way in the first state.

The second state of the legs 676 is activated when the drug delivery device (and with it the button assembly) falls down and hits a floor (or wall) 690 by the plate-like button body 670 thereby producing a shock force. In this case, as shown in FIG. 15, the gravity force drives the heavy metal sphere 697 into downwards direction leading to a compression of the compression spring 698. Thereby, the metal sphere 697 is driven out of its seat 699 and allows that the legs 676 move towards each other. As it is explained above in this state there is no transmission of axial force from the plate—like element 670 to the driven element 695 of the drug delivery device.

Accordingly, in a first state shown in FIGS. 13 and 14 the acceleration sensor within the recess 676 a of the stem is in its first state allowing a force transmission of an axial force acting at the touch surface 670*a* to the driven element 695 of the drug delivery device. Accordingly, the axial force (see arrows 679 in FIG. 14) provided by the user pressing the plate-like button body 670 at its touch surface 670*b* is transmitted via the stem 675 to the driven element 695 of the drug delivery device.

In case the drug delivery device falls down and hits the floor 690 (or wall) the acceleration sensor (metal sphere 697, compression spring 698) is activated and prevents a force transmission of an axial shock force acting at the touch surface 670*a* and caused by the floor 690 (or wall) to the driven element 695 of the drug delivery device (see FIG. 15).

The embodiments of FIGS. 10 to 15 also refer to the general construction of the drug delivery device shown in FIGS. 1 to 3 and explained with reference to these Figures.

Figures 16, 17, 18:
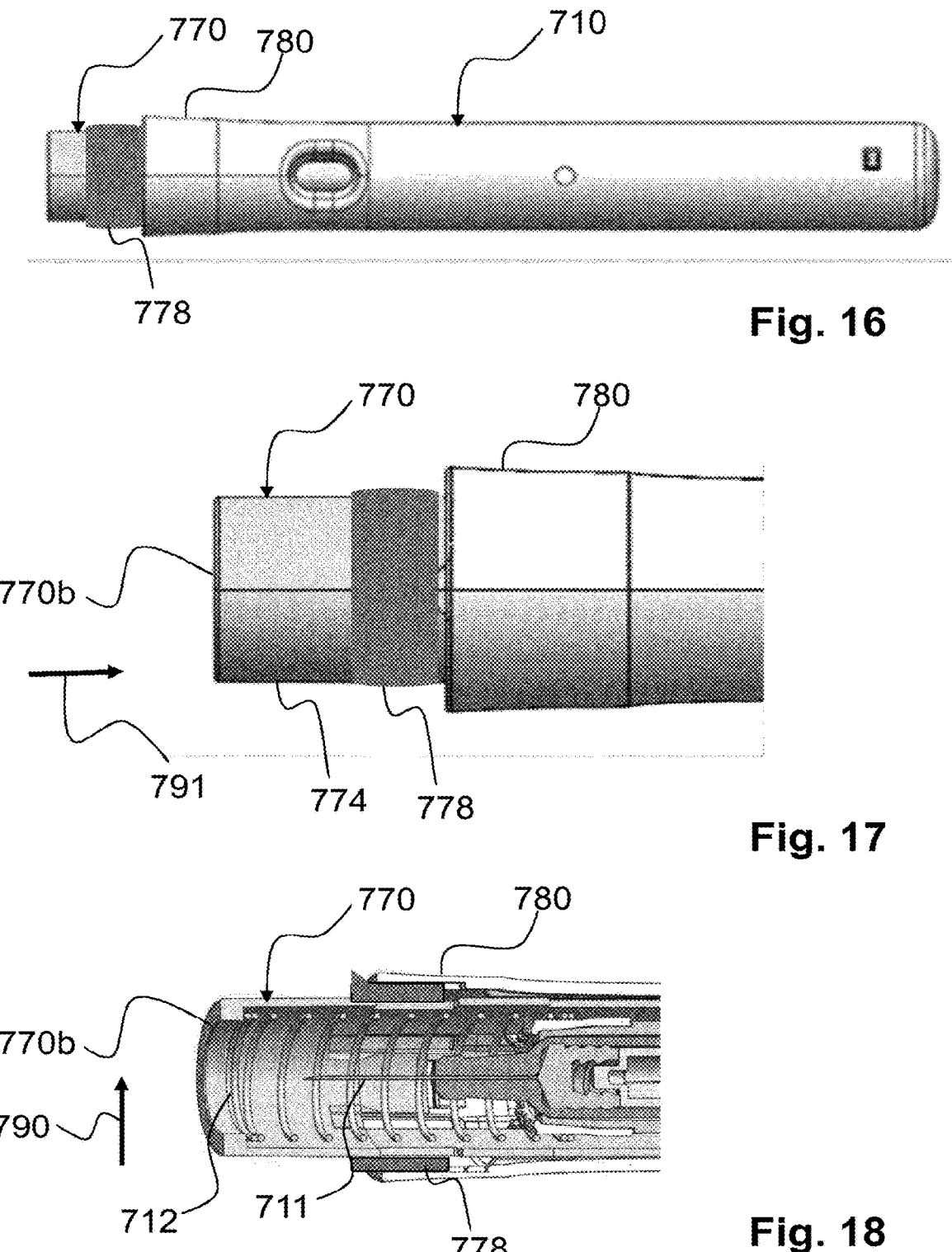
FIG. 16 shows a side view of an autoinjector with a third embodiment of a button assembly.
FIG. 17 shows a distal section of FIG. 16 in an initial state.
FIG. 18 shows a sectional view of FIG. 17 in a locked state.

FIGS. 16 to 18 show another embodiment of a button assembly which is, for example, suitable for a drug delivery device in form of an autoinjector. The autoinjector depicted in FIG. 16 comprises a housing 710 and a sleeve-like button body 770 forming a shield for needle 711. The sleeve-like button body 770 further comprises a touch surface 770*b* which is used to place the autoinjector on the patient's skin when the medicament dose is to be injected. In order to initiate the injection, the patient presses the autoinjector onto the skin such that the sleeve-like button body 770 (needle shield) is retracted from its initial position and moved longitudinally against the spring force of an activation spring 712 (e.g. in proximal direction) in order to expose the needle and pierce the skin. Additionally, the movement of the sleeve-like button body 770 activates the drive mechanism accommodated within the housing 710, for example by the movement of the sleeve-like button body a pre-tensioned drive spring is released thereby driving a drive element in order to eject the pre-defined dose. The construction and the principles of operation of sleeve-triggered and button-triggered autoinjectors are assumed to be well-known and have been, for example, explained in WO 2012/110577 A1 and WO 2012/110577 A1, respectively, whereof the entire disclosure shall be incorporated herein by means of reference.

The sleeve-like button body 770 comprises a material composite with at least one first material component consisting of the first material as indicated above and at least one second material component consisting of a second material as indicated above and different from the first material and having a higher elasticity and/or plasticity than the first material. The second material component forms a ring-like circumferential section 778 of a side surface 774 of the sleeve-like button body 770. The ring-like section 778 has a larger outer diameter than the remaining side surface 774 of the sleeve-like button body 770 forming the first material component. The second material component forms a compressible or collapsible segment. The ring-like section 778 is arranged in a region close to (i.e. in a short distance to) a distal end 780 of the housing 710 which forms the support element, referring to an extended position of the sleeve-like button body 770 shown in FIGS. 16 and 17.

This embodiment works such that if the button assembly observes a shock force, for example with a force component transversal to the longitudinal direction of the button assembly (see arrow 790 in FIG. 18), the the support element (distal end 780 of the housing 710) and the ring-like section 778 with the deformable or compressible second material component become wedged together such that the sleeve-like button body 770 cannot move into longitudinal direction as shown in FIG. 18. The proximal end of the support element, e.g. an edge of the support element, penetrates the deformable second material by deformation and thereby blocks the axial movement of the sleeve-like button body. Accordingly, medication dose ejection is prevented. In contrast, if the user presses the sleeve-like button body 770 (needle shield) in longitudinal direction (see arrow 791 in FIG. 17) as planned in order to expose the needle 711 and eject the pre-defined dose the sleeve-like button body 770 moves longitudinally into the housing 710 without interaction with its distal end 780 thereby activating the drive mechanism. This is because the outer diameter of the ring-like section 778 is less than the inner diameter of the support element (distal end 780 of the housing 710).

Figure 19:
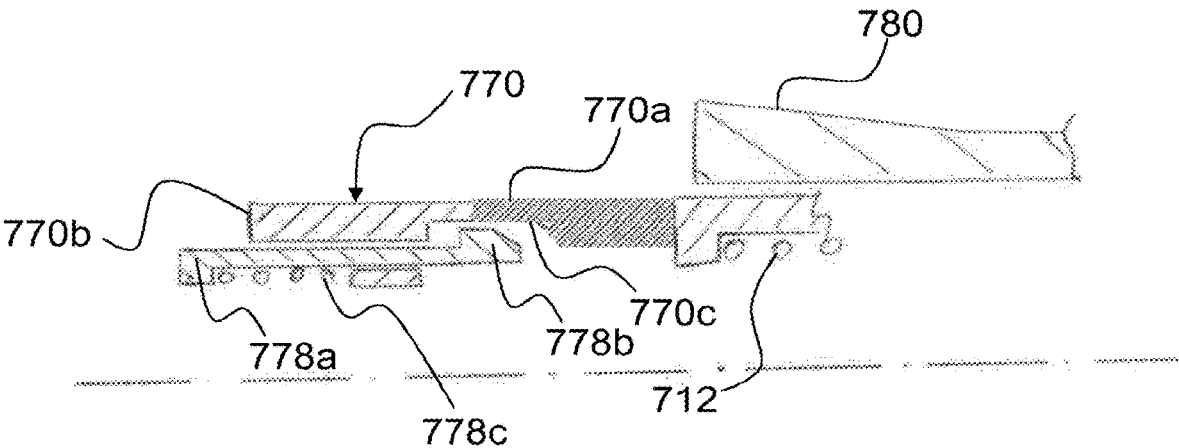
FIG. 19 shows a sectional view of a fourth embodiment of a button assembly.

An other embodiment which corresponds with the embodiment shown in FIGS. 16 to 18 beside the deactivation mechanism is depicted in FIG. 19. The deactivation mechanism of this embodiment comprises an additional sleeve member (e.g. a hollow cylinder) accommodated within the sleeve-like button body 770 at its distal end. The additional sleeve member is referred to as the actuation sleeve 778*a* in the following. The actuation sleeve 778*a* comprises a rim 778*b* projecting from the outer surface of the actuation sleeve 778*a* at its proximal end forming an actuation feature. The rim 778*b* is engaged with the sleeve-like button body 770 within a corresponding recess 770*c* at the inner surface of the sleeve-like button body 770. The actuation sleeve 778*a* is movable into longitudinal direction against the force of a spring 778*c* and is axially guided by the sleeve-like button body 770. Initially, the actuation sleeve 778*a* projects from the distal end of the sleeve-like button body 770. Further, the sleeve-like button body 770 comprises a bendable segment 770*a* which belongs to the deactivation mechanism and is accommodated close to (i.e. within a short distance to) or overlapping with the support element (the distal end 780 of the housing 710). The bendable segment forms a second material component, wherein the remaining section of the sleeve-like button body 770 forms a first material component as defined above. In case of an impact event by a shock force the actuation sleeve 778*a* is forced to move relative to the sleeve-like button body 770 into the longitudinal direction as it forms the distal-most end of the button assembly, pushes the actuation sleeve 778*a* out of engagement with the sleeve-like button body 770 and thereby deforms the sleeve-like button body 770 in the bendable segment 770*a* outwards such that the bendable segment 770*a* and the distal end of the support element (distal end 780 of the housing 710) become wedged together thereby blocking the axial movement of the sleeve-like button body 770 because the spring 778*c* is weaker than the activation spring 712. The bendable segment 770*a* consists of the second material as indicated above, whereas the remaining section of the sleeve-like button body consists of the first material as indicated above. For normal injection the patient longitudinally presses the actuation sleeve 778*a* and the sleeve-like button body with his/her skin into proximal direction without considerably deforming the bendable segment 770*a*. Accordingly, the sleeve-like button body 770 is not prevented to move by the bendable segment 770*a*.

REFERENCE NUMERALS

10 housing (casing)
11 spline tooth
12 insert
20 cartridge holder
30 piston rod (lead screw)
40 drive sleeve
41 crown tooth 42 spline tooth
50 nut
60 dose setting element
60a number sleeve lower
60b number sleeve upper
70 button
70a sleeve section
70b touch surface
72 central stem
75 central projection
80 dose selector
90 torsion spring
100 cartridge
110 gauge element
120 clutch plate
121 crown tooth
130 clutch spring
140 bearing
220, 320, 420 clutch plate
270, 370, 470 button
270a, 370a, 470a sleeve section
270b, 370b, 470b touch surface
270d, 270e coupling plane
370d, 370e coupling plane
271, 371 ring-like cladding element
272 central conical element
275, 375, 475 projection
278 conical ring-like element
372 central cylindrical element
373, 374 cross member
378 polyhedral element
470d coupling plane
471 plate-like element
478 cap
280, 380, 480 dose selector
570, 670 plate-like button body (button)
570b, 670b touch surface
570d coupling plane
571 central section
574 side surface
578 ring-like outer section
573, 673 rim
575, 675 central stem
579, 679 arrow
580, 680 dose selector
581, 681 through hole
582, 682 coil spring
584, 684 distal wall surface
585, 685 proximal end section of the dose selector 580
590, 690 floor
586, 686 stop surface
676 leg
676a recess
676b outer projection (step surface)
695 driven element
696 recess of driven element
697 metal sphere
698 compression spring
699 seat (resting position)
710 housing
711 needle
712 activation spring
770 sleeve-like button body (needle shield)
770a bendable segment of the sleeve-like button body 770
770b touch surface
770c recess
774 side surface of the sleeve-like button body 778 ring-like section
778a actuation sleeve
778b rim
778c spring
780 distal end of the housing 710 (support member)
790, 791 arrow

The invention claimed is:

1. A button for a drug delivery device, the button comprising:
a button body forming a touch surface;
wherein the button body is adapted to be coupled by an axial supporting member to a noise-generating interface of the drug delivery device and to be movable in a longitudinal direction of the drug delivery device;
wherein the button body comprises a material composite comprising at least two first material components consisting essentially of a first material and at least one second material component consisting essentially of a second material different from the first material, wherein one of the at least two first material components is formed by a ring-like cladding element shaped to form a main part of the touch surface of the button, another of the at least two first material components is formed by a central conical element, and the at least one second material component is formed by a conical ring-like element accommodated between the ring-like cladding element and the central conical element; and
wherein one of the at least two first material components and the at least one second material component are coupled via at least one coupling plane that is slanted or perpendicular to the longitudinal direction.

2. The button of claim 1, wherein the first material has a higher compressive strength than the second material and/or a higher inner sound damping than the second material and/or a lower viscosity than the second material.

3. The button of claim 1, wherein the at least one coupling plane runs between the touch surface and the axial supporting member.

4. The button of claim 1, wherein the axial supporting member is formed by one of the at least two first material components.

5. The button of claim 1, wherein the drug delivery device is configured to produce a noise or a vibration, and the axial supporting member is configured to transmit the noise or the vibration to the touch surface.

6. The button of claim 1, wherein the axial supporting member is formed by a projection projecting from one of the at least two first material components in the longitudinal direction.

7. A drug delivery device, comprising:
a body; and
a button assembly secured to the body, the button assembly comprising:
a button body forming a touch surface;
wherein the button body is adapted to be coupled by an axial supporting member to a noise-generating interface of the drug delivery device and to be movable in a longitudinal direction of the drug delivery device;
wherein the button body comprises a material composite comprising at least two first material components consisting essentially of a first material and at least one second material component consisting essentially of a second material different from the first material, wherein one of the at least two first material components is formed by a ring-like cladding ele-
ment shaped to form a main part of the touch surface
of the button assembly, another of the at least two
first material components is formed by a central
conical element, and the at least one second material
component is formed by a conical ring-like element
accommodated between the ring-like cladding ele-
ment and the central conical element; and
wherein one of the at least two first material compo-
nents and the at least one second material component
are coupled via at least one coupling plane that is
slanted or perpendicular to the longitudinal direction.

8. The drug delivery device of claim 7, comprising a drive
mechanism, wherein the drive mechanism comprises the
button assembly.

9. The drug delivery device of claim 7, wherein the
second material comprises a higher elasticity and/or plas-
ticity than the first material; and
wherein the second material at least partially forms the
touch surface of the button body or an inner surface of
the button body.

10. The drug delivery device of claim 7, wherein the drug
delivery device is configured to produce a vibration, and the
button assembly is configured to transmit the vibration to the
touch surface.

11. The drug delivery device of claim 7, further compris-
ing a cartridge containing a medicament.

* * * * *